(12) United States Patent
Crucs

(10) Patent No.: US 8,265,729 B2
(45) Date of Patent: Sep. 11, 2012

(54) THIRD PARTY ACQUISITION OF IMAGES AT THE DIRECTION OF AN INDEPENDENT IMAGING APPLICATION

(75) Inventor: Kevin M. Crucs, Copley, OH (US)

(73) Assignee: Apteryx, Inc., Akron, OH (US)

( * ) Notice: Subject to any disclaimer, the term of this patent is extended or adjusted under 35 U.S.C. 154(b) by 365 days.

(21) Appl. No.: 12/639,143

(22) Filed: Dec. 16, 2009

(65) Prior Publication Data

US 2010/0123831 A1 May 20, 2010

Related U.S. Application Data

(63) Continuation-in-part of application No. 11/078,810, filed on Mar. 11, 2005.

(51) Int. Cl.
*A61B 5/05* (2006.01)
(52) U.S. Cl. ........................................ 600/407; 382/128
(58) Field of Classification Search .......... 600/407–424, 600/437–480; 382/128–132
See application file for complete search history.

(56) References Cited

U.S. PATENT DOCUMENTS

| | | | |
|---|---|---|---|
| 3,849,596 A | | 11/1974 | Lawrence |
| 4,941,164 A | | 7/1990 | Schuller et al. |
| 5,179,579 A | * | 1/1993 | Dove et al. ........................ 378/38 |
| 5,381,457 A | | 1/1995 | Burns |
| 5,572,566 A | * | 11/1996 | Suzuki et al. ................. 378/98.2 |
| 7,286,954 B2 | * | 10/2007 | Kopelman et al. ............ 702/152 |
| 8,041,091 B2 | * | 10/2011 | de Oliveira e Ramos et al. .............................. 382/128 |
| 2003/0065523 A1 | | 4/2003 | Pruche et al. |
| 2007/0214017 A1 | * | 9/2007 | Profio et al. ....................... 705/3 |

* cited by examiner

*Primary Examiner* — Sanjay Cattungal
(74) *Attorney, Agent, or Firm* — Hahn Loeser & Parks LLP

(57) ABSTRACT

A system and method for capturing and displaying images in an ordered manner. An image progression description (IPD) is generated using an imaging software application (ISA). The IPD defines an ordered sequence of image acquisition instruction sets (IAIS) and an image display layout (IDL). The ordered sequence of IAIS is transferred to a portable image acquisition device (PIAD) which reads and sequentially displays the ordered sequence of IAIS. A plurality of images is acquired using the PIAD in accordance with the ordered sequence of IAIS. The plurality of images are transferred back to the ISA and are displayed according to the IDL.

21 Claims, 14 Drawing Sheets

Fig. 4

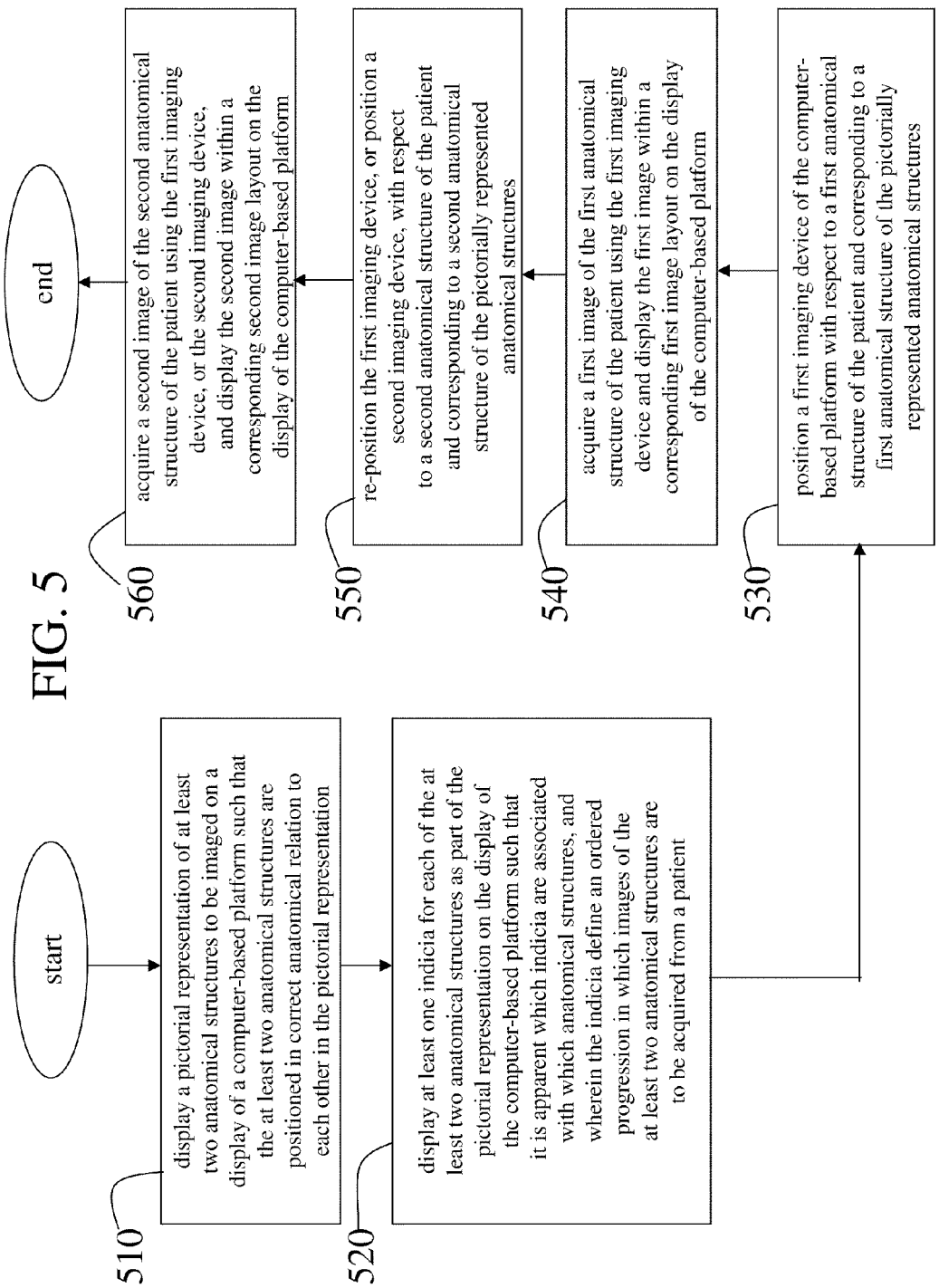

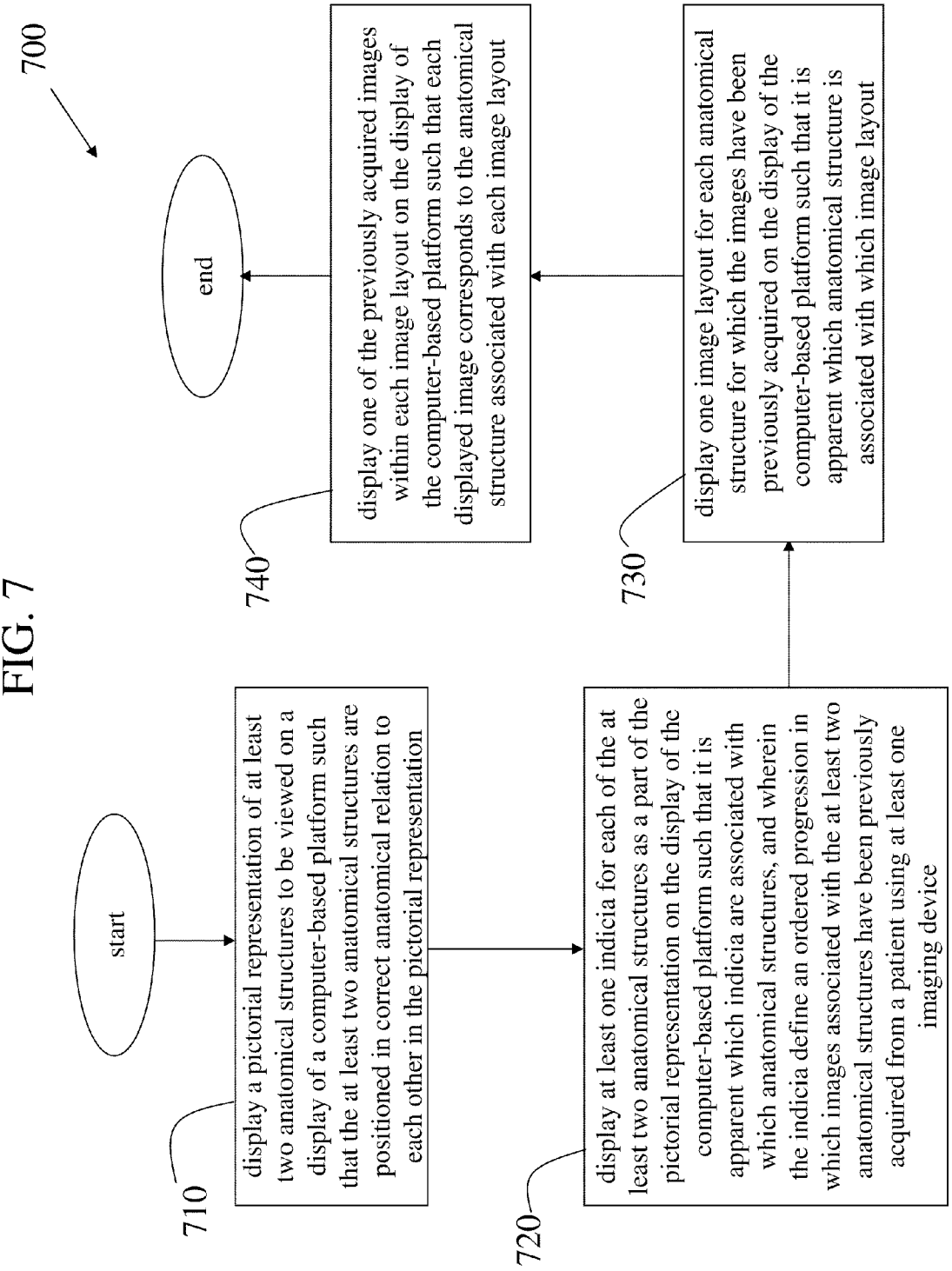

FIG. 13

Example Ordered Sequence of Image Acquisition Instruction Sets (IAIS)
(4 Bite Wing Series)

1301 —
Image Acq. No.: #1
Anatomic Region: teeth # 1, 2, 3, 30, 31, 32
Orientation: up 1302 —
Image Acq. No.: #2
Anatomic Region: teeth # 4, 5, 6, 27, 28, 29
Orientation: up 1303 —
Image Acq. No.: #3
Anatomic Region: teeth # 14, 15, 16, 17, 18, 19
Orientation: up 1304 —
Image Acq. No.: #4
Anatomic Region: teeth # 11, 12, 13, 20, 21, 22
Orientation: up

1300

THIRD PARTY ACQUISITION OF IMAGES AT THE DIRECTION OF AN INDEPENDENT IMAGING APPLICATION

This U.S. patent application is a continuation-in-part of U.S. patent application Ser. No. 11/078,810 filed on Mar. 11, 2005, which is incorporated herein by reference in its entirety.

TECHNICAL FIELD

Certain embodiments of the present invention relate to digital imaging. More particularly, certain embodiments of the present invention relate to a system and methods for relaying instructions on how to capture a sequence of images to independent batch acquisition devices, and how to subsequently view the captured images.

BACKGROUND

Today, medical imaging technicians need to know about a medical procedure or exam that is to be performed, and they need to remember an order in which a doctor wants images acquired for the procedure or exam. Acquisitions are not always the same from exam to exam and it is not always easy for a technician to remember the desired order of acquisition. Furthermore, doctors don't want to have to remember the acquisition order they prescribed, and they don't want to necessarily receive and view the acquired images in the order in which they were acquired. Other fields of endeavor such as, for example, construction and structural inspection have similar image acquisition and viewing issues.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY

A first embodiment of the present invention provides a method of capturing and displaying images in an ordered manner. The method includes generating an image progression description (IPD) using an imaging software application (ISA) running on a processor-based hardware platform (PBHP). The image progression description (IPD) defines an ordered sequence of image acquisition instruction sets (IAIS) and an image display layout (IDL). The method further includes transferring at least said ordered sequence of image acquisition instruction sets (IAIS) portion of said image progression description (IPD) to a portable image acquisition device (PIAD). The method also includes the portable image acquisition device (PIAD) reading at least the transferred ordered sequence of image acquisition instruction sets (IAIS) portion of the image progression description (IPD) and sequentially displaying each instruction set of the ordered sequence of image acquisition instruction sets (IAIS). The method further includes acquiring a single image, using the portable image acquisition device (PIAD), in accordance with each instruction set of the ordered sequence of image acquisition instruction sets (IAIS), thereby acquiring a plurality of images. The method also includes transferring the plurality of images to the processor-based hardware platform (PBHP), and displaying the plurality of images according to the image display layout (IDL). The method may further include the imaging software application (ISA) associating the plurality of images with the image display layout (IDL) based on an identifying code with which the plurality of images and the image progression description (IPD) are each electronically tagged. The method may also include the imaging software application (ISA) electronically tagging the image progression description (IPD) with an identifying code before the image progression description (IPD) is transferred. The method may further include the portable image acquisition device (PIAD) electronically tagging the plurality of images with the identifying code before the plurality of images are transferred. The plurality of images may be transferred via a batch transfer process, or via a real time transfer process subsequent to acquiring each single image and before acquiring a next single image of the plurality of images. Each instruction set of the ordered sequence of image acquisition instruction sets (IAIS) may include an image acquisition number, identification of an anatomic region to be imaged, and acquisition orientation information, for example. Similarly, each instruction set of the ordered sequence of image acquisition instruction sets (IAIS) may include an image acquisition number, identification of a structural region to be imaged, and acquisition orientation information, for example. The processor-based hardware platform (PBHP) may be co-located with the portable image acquisition device (PIAD), or may be located remotely from the portable image acquisition device (PIAD).

Another embodiment of the present invention comprises a system for capturing and displaying images in an ordered manner. The system includes means for generating an image progression description (IPD). The image progression description (IPD) defines an ordered sequence of image acquisition instruction sets (IAIS) and an image display layout (IDL). The system further includes means for transferring at least the ordered sequence of image acquisition instruction sets (IAIS) portion to the image progression description (IPD). The system also includes means for reading at least the transferred ordered sequence of image acquisition instruction sets (IAIS) portion of the image progression description (IPD) and sequentially displaying each instruction set of the ordered sequence of image acquisition instruction sets (IAIS). The system further includes portable means for acquiring a single image in accordance with each instruction set of the ordered sequence of image acquisition instruction sets (IAIS), thereby allowing acquisition of a plurality of images. The system also includes means for transferring the plurality of images, and means for displaying the plurality of images according to the image display layout (IDL). The system may further include means for associating the plurality of images with the image display layout (IDL) based on an identifying code with which the plurality of images and the image progression description (IPD) are each electronically tagged. The system may also include means for electronically tagging the image progression description (IPD) with an identifying code before the image progression description (IPD) is transferred. The system may further include means for electronically tagging the plurality of images with the identifying code before the plurality of images are transferred. The means for transferring the plurality of images may employ a batch transfer process, or a real time transfer process wherein each single image of the plurality of images is transferred subsequent to acquiring each single image and before acquiring a next single image of the plurality of images. Each instruction set of the ordered sequence of image acquisition instructions sets (IAIS) may include an image acquisition number, identification of an anatomic region to be imaged, and acquisition orientation information, for example. Similarly, each instruction set of the ordered sequence of image acquisition instructions sets (IAIS) may include an image acquisition number, identification of a structural region to be imaged, and acquisition orientation information, for example. The means for generating an image progression description (IPD) may be co-located with the portable means for acquiring. The portable means for acquiring may be located remotely from the means for generating an image progression description. The means for reading and sequentially displaying may be co-located with the portable means for acquiring.

These and other advantages and novel features of the present invention, as well as details of an illustrated embodiment thereof, will be more fully understood from the following description and drawings.

BRIEF DESCRIPTION OF THE DRAWINGS

FIG. 4 illustrates an embodiment of a screen displayed by the system of FIG. 1 showing ten choices of progressions icons, in accordance with various aspects of the present invention;

FIG. 5 illustrates a flow chart of an embodiment of a method for capturing a sequence of anatomical images using the computer-based platform of FIG. 1, in accordance with various aspects of the present invention;

FIG. 7 illustrates a flow chart of an embodiment of a method for viewing a sequence of previously captured anatomical images on the computer-based platform of FIG. 1, in accordance with various aspects of the present invention;

FIG. 13 illustrates an example embodiment of an ordered sequence of image acquisition instruction sets (IAIS) generated using the system of FIG. 10 and the method of FIG. 12.

DETAILED DESCRIPTION

Figure 1:
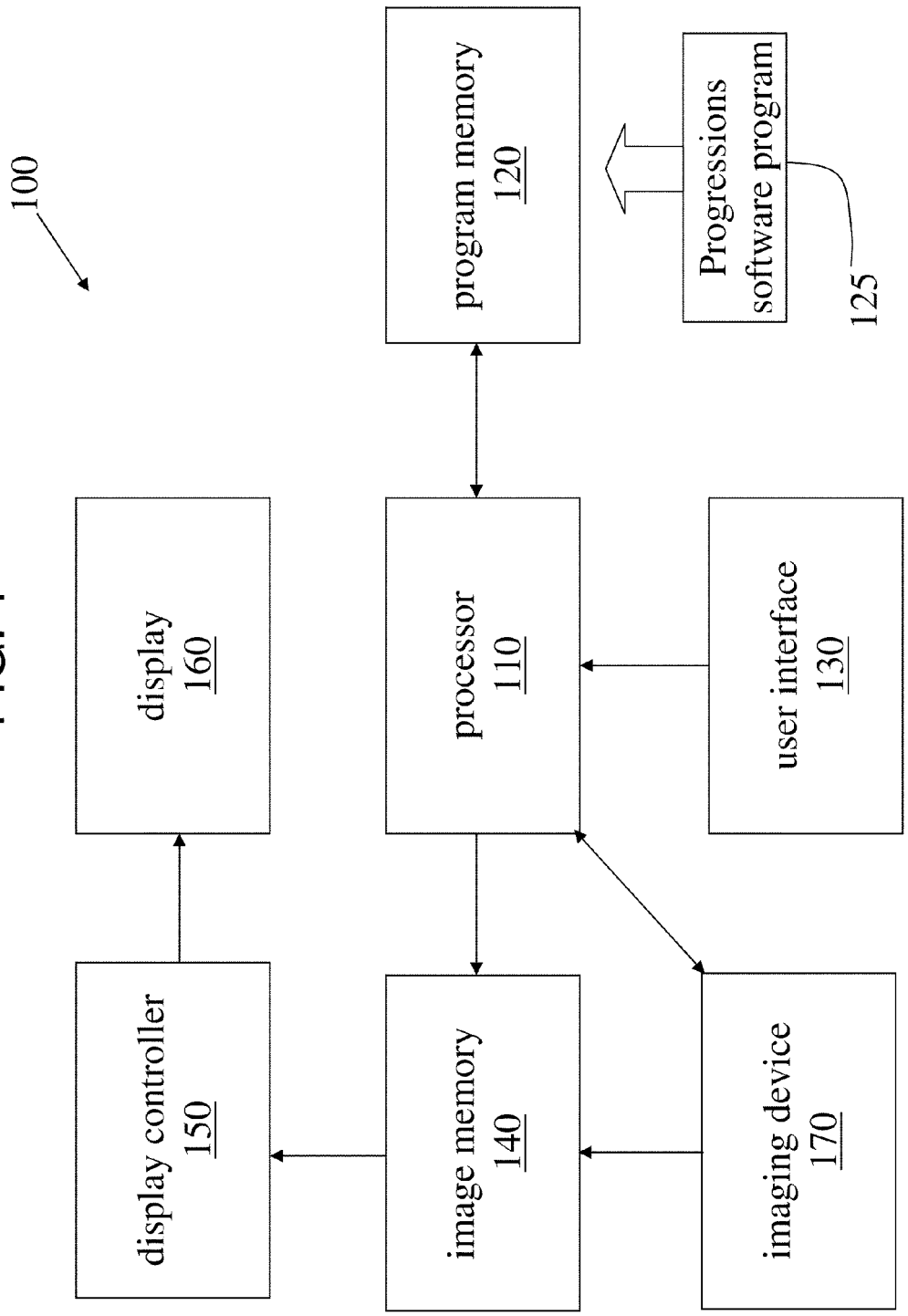
FIG. 1 is a schematic block diagram of an exemplary embodiment of a computer-based system for capturing and displaying progressions of anatomical images, in accordance with various aspects of the present invention.

FIG. 1 is a schematic block diagram of an exemplary embodiment of a computer-based system 100 (e.g., a PC-based platform) for capturing and displaying progressions of anatomical images, in accordance with various aspects of the present invention. The system 100 comprises a processor 110, a program memory 120 storing a progressions software program 125, a user interface 130, an image memory 140, a display controller 150, a display 160, and an imaging device 170.

The processor 110 interfaces to the program memory 120 and executes the progressions software program 125. The user interface 130 connects to the processor 110 to allow a user of the system 100 to select and control various functions of the system 100. The image memory 140 interfaces to the processor 110 to store image data to be displayed. The display controller 150 interfaces to the image memory 140 to extract image data from the image memory in a controlled manner and convert the image data to video data. The display 160 interfaces to the display controller 150 to accept video data from the display controller 150 such that the video data is presented to a user on the display 160. The imaging device 170 interfaces to the processor 110 and the image memory 170.

The progressions software program 125 is the executable program to run the system 100. The user interface 130 may comprise, for example, a keyboard, a mouse, a touch-screen (i.e., the user interface 130 is combined with the display 160), or push buttons. The functionality controlled through the user interface 130 includes, for example, selecting a progression of image shots, selecting an individual image shot, and capturing a digital image.

As an example, a user (e.g., a dentist) may want to take an image of a tooth of a patient using the system 100. The dentist aligns the imaging device 170 (e.g., a digital X-ray device) with a tooth of the patient and presses a button on the user interface 130 to administer an X-ray dose from the device 170 and capture a resultant digital image (i.e., image shot) of the tooth in the image memory 140. In accordance with an embodiment of the present invention, the captured digital image is stored in the image memory 140 as a designated image shot of a predefined progression of image shots for the patient. For example, the progression of image shots may correspond to a bite wing series of the patient. The dentist may continue in a similar manner to complete the capturing of a plurality of image shots to complete the bite wing series progression.

In accordance with various embodiments of the present invention, the imaging device 170 may comprise any digital imaging device including any one of, for example, an intra-oral digital X-ray device, an intra-oral digital camera, and an intra-oral digital video camera. Other imaging devices are possible as well for imaging teeth or other types of anatomy (e.g., an MRI imaging device, a luminescence imaging device, an electrical potential imaging device).

Figure 2:
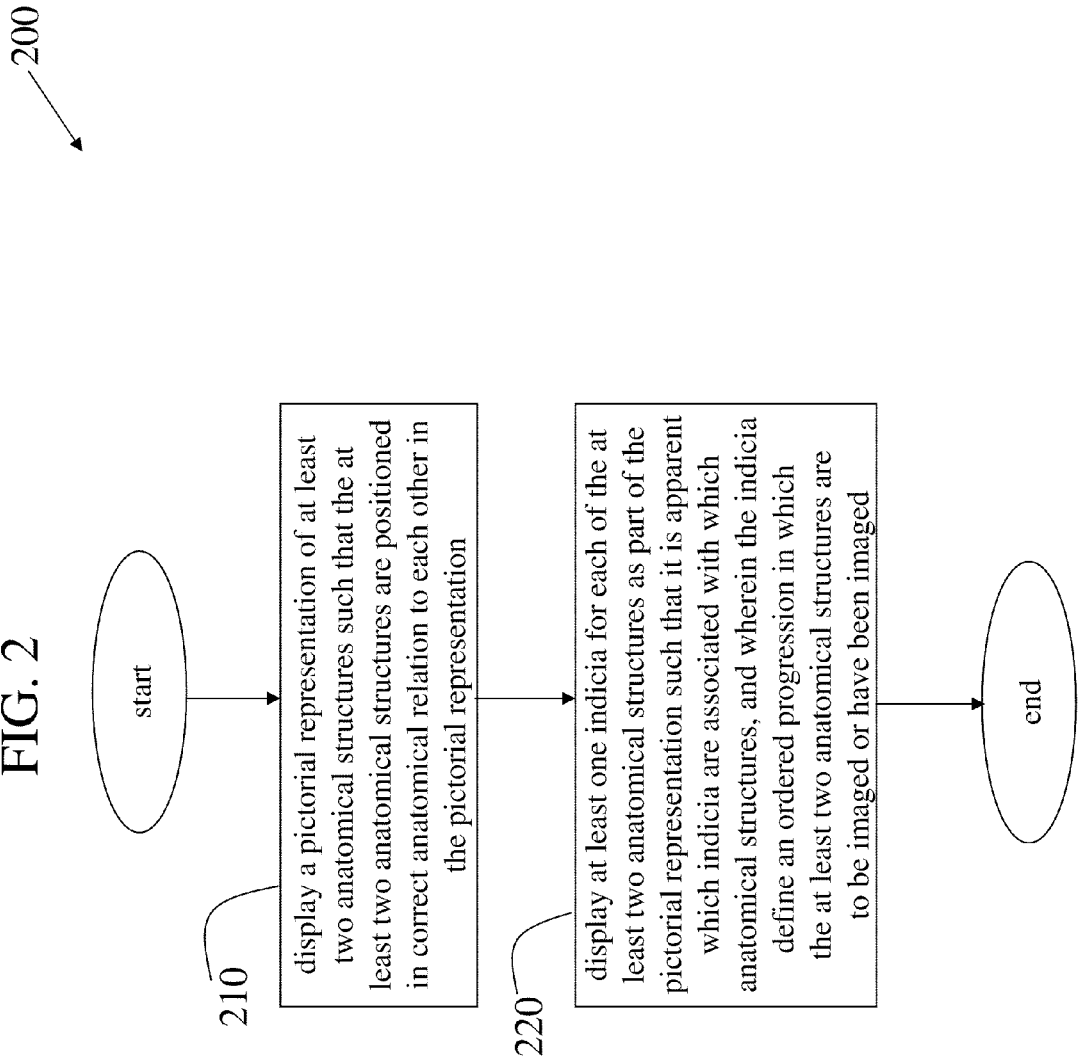
FIG. 2 is a flowchart of an embodiment of a method of graphically representing a sequence of anatomical structures to be imaged or which have been imaged using the system of FIG. 1, in accordance with various aspects of the present invention.

FIG. 2 is a flowchart of an embodiment of a method 200 of graphically representing a sequence of anatomical structures to be imaged or which have been imaged using the system 100 of FIG. 1, in accordance with various aspects of the present invention. In step 210, a pictorial representation of at least two anatomical structures is displayed such that the at least two anatomical structures are positioned in correct anatomical relation to each other in the pictorial representation. In step 220, at least one indicia is displayed for each of the at least two anatomical structures as a part of the pictorial representation such that it is apparent which indicia are associated with which anatomical structures. Also, the indicia define an ordered progression in which the at least two anatomical structures are to be imaged or have been imaged.

Figure 3:
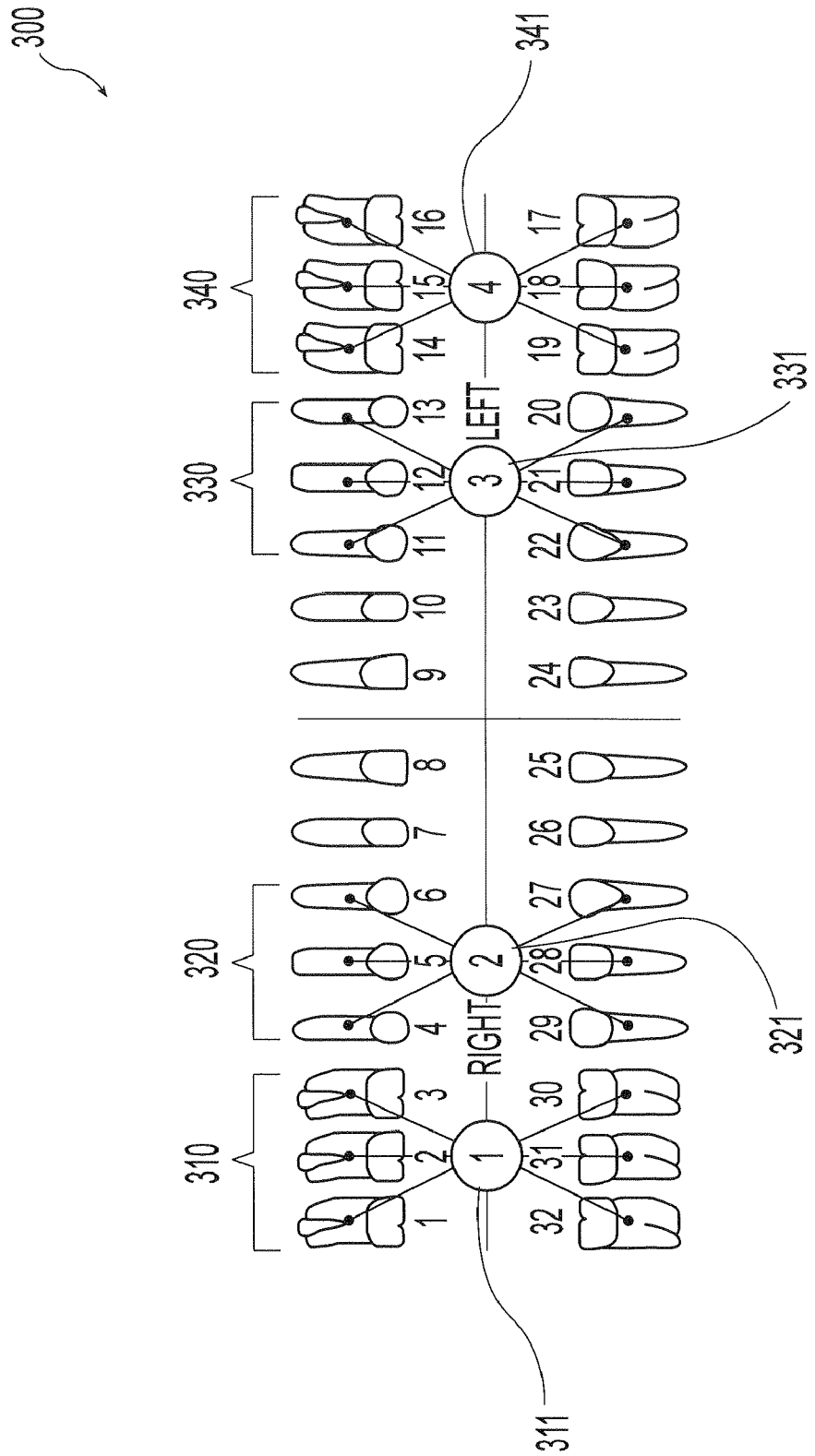
FIG. 3 illustrates an exemplary embodiment of a graphical representation of a sequence of anatomical structures generated and displayed by the system of FIG. 1 using the method of FIG. 2, in accordance with various aspects of the present invention.

FIG. 3 illustrates an exemplary embodiment of a graphical representation of a sequence of anatomical structures generated and displayed by the system 100 of FIG. 1 using the method 200 of FIG. 2, in accordance with various aspects of the present invention. The graphical representation of FIG. 3 represents a 4 Bite Wing Series of a tooth progression chart 300. The tooth progression chart 300 shows all 32 human adult teeth in correct anatomical relation to each other. Also, FIG. 3 shows a pictorial representation of a sequence or progression of four anatomical structures (i.e., four sets of teeth) 310, 320, 330, and 340 corresponding to the standard adult 4 Bite Wing Series. Each anatomical structure (310, 320, 330, 340) has associated with it a corresponding indicia (311, 321, 331, 341). Each indicia clearly indicates which teeth correspond to which anatomical structure. Note that the pictorial representations of the anatomical structures (i.e. teeth) actually look like those anatomical structures (i.e. teeth). The pictorial representations are not simply iconic symbols such as intra-oral radiograph holders.

For example, the teeth numbers 1, 2, 3, 30, 31, and 32 correspond to indicia 311. Indicia 311 includes a circled number 1 with connecting lines extending from the circled number 1 to the individual teeth (teeth numbers 1, 2, 3, 30, 31, and 32). Therefore, the six teeth (teeth numbers 1, 2, 3, 30, 31, and 32) constitute a first anatomical structure 310. The number 1 of the indicia 311 also indicates that this first anatomical structure 310 is the first anatomical structure and shot number in the defined 4 Bite Wing Series progression.

Similarly, anatomical structure 320 corresponds to the teeth numbers 4, 5, 6, 27, 28, and 29 as indicated by indicia 321 and is the second anatomical structure in the progression. Anatomical structure 330 corresponds to the teeth numbers 11, 12, 13, 20, 21, and 22 as indicated by indicia 331 and is the third anatomical structure in the progression. Anatomical structure 340 corresponds to the teeth numbers 14, 15, 16, 17, 18, and 19 as indicated by indicia 341 and is the fourth anatomical structure in the progression. Each defined anatomical structure (310, 320, 330, and 340) may have an image shot (i.e., a digital image) associated with it.

The indicia 311, 321, 331, and 341 each include a numeric character. However, in accordance with various alternative embodiments of the present invention, other representations are possible as well, including alphabetic characters (e.g., A, B, C, D) and alpha-numeric characters (e.g., 1A, 1B, 1C, 1D).

Figure 4:
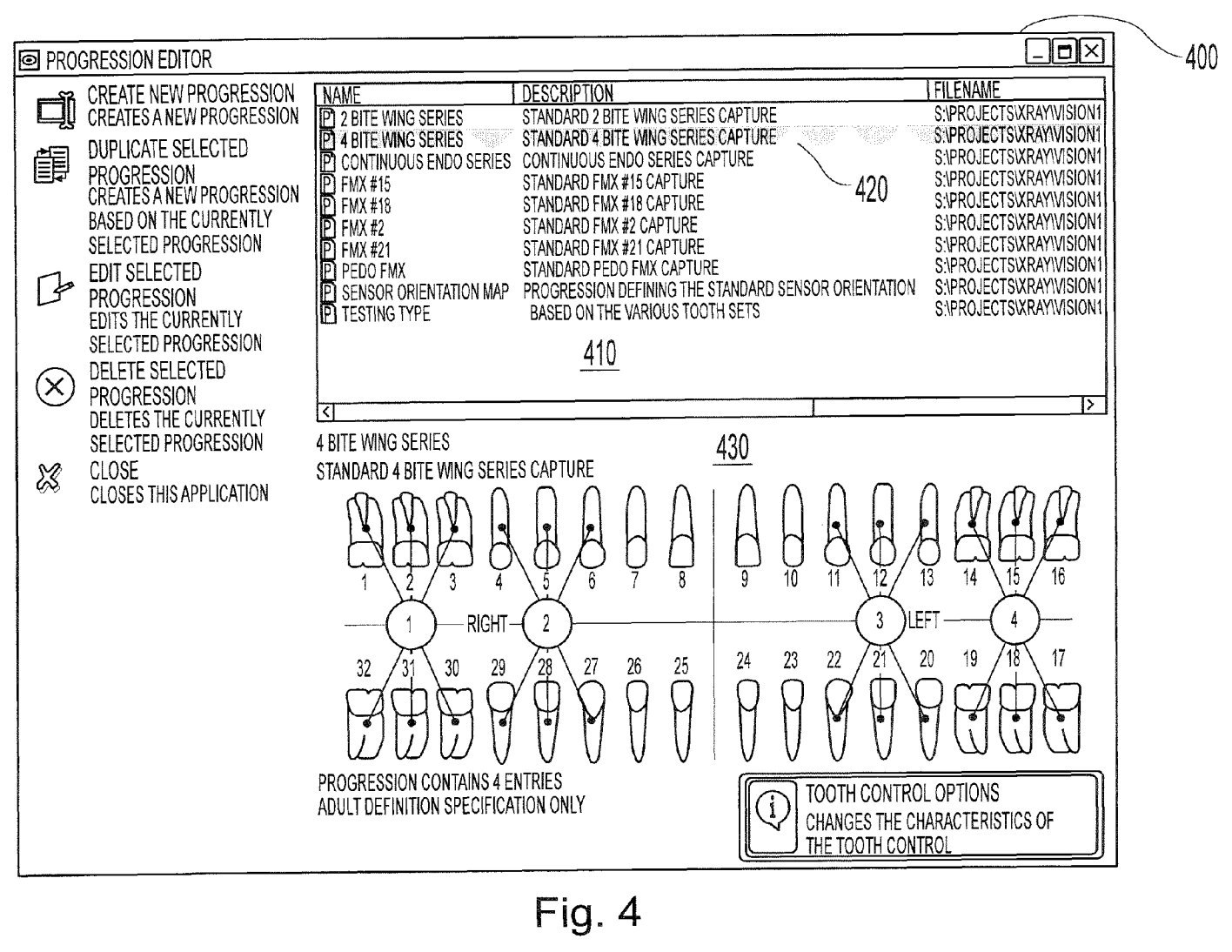

FIG. 4 illustrates an embodiment of a screen 400 displayed by the system 100 of FIG. 1 showing ten choices of progressions icons, in accordance with various aspects of the present invention. The ten choices correspond to a stored list of progression series that may be called up to appear in a window 410 of the screen 400. Each progression series is defined by two or more anatomical structures and associated indicia. Each indicia defines which teeth are associated with which anatomical structure as well as the orientation of any associated image shot. The second choice 420, which is the 4 Bite Wing Series progression, is hi-lighted and displayed as a tooth progression chart 430.

FIG. 5 illustrates a flow chart of an embodiment of a method 500 for capturing a sequence of anatomical images using the computer-based platform 100 of FIG. 1, in accordance with various aspects of the present invention. In step 510, a pictorial representation of at least two anatomical structures to be imaged are displayed on a display of a computer-based platform such that the at least two anatomical structures are positioned in correct anatomical relation to each other in the pictorial representation. In step 520, at least one indicia is displayed for each of the at least two anatomical structures as a part of the pictorial representation on the display of the computer-based platform such that it is apparent which indicia are associated with which of the anatomical structures. Also, the indicia define an ordered progression in which images of the at least two anatomical structures are to be acquired from a patient. The exact order of the steps 510-520 is not necessarily critical. Other embodiments may re-order and/or combine the steps to achieve a same resultant displayed screen. In step 530, a first imaging device of the computer-based platform is positioned with respect to a first anatomical structure of the patient and corresponding to a first anatomical structure of the pictorially represented anatomical structures. In step 540, a first image of the first anatomical structure of the patient is acquired using the first imaging device and the first image is displayed within a corresponding first image layout on the display of the computer-based platform. In step 550, the first imaging device is repositioned, or a second imaging device is positioned, with respect to a second anatomical structure of the patient and corresponding to a second anatomical structure of the pictorially represented anatomical structures. In step 560, a second image of the second anatomical structure of the patient is acquired using the first imaging device, or the second imaging device, and the second image is displayed within a corresponding second image layout on the display of the computer-based platform.

Figure 6A:
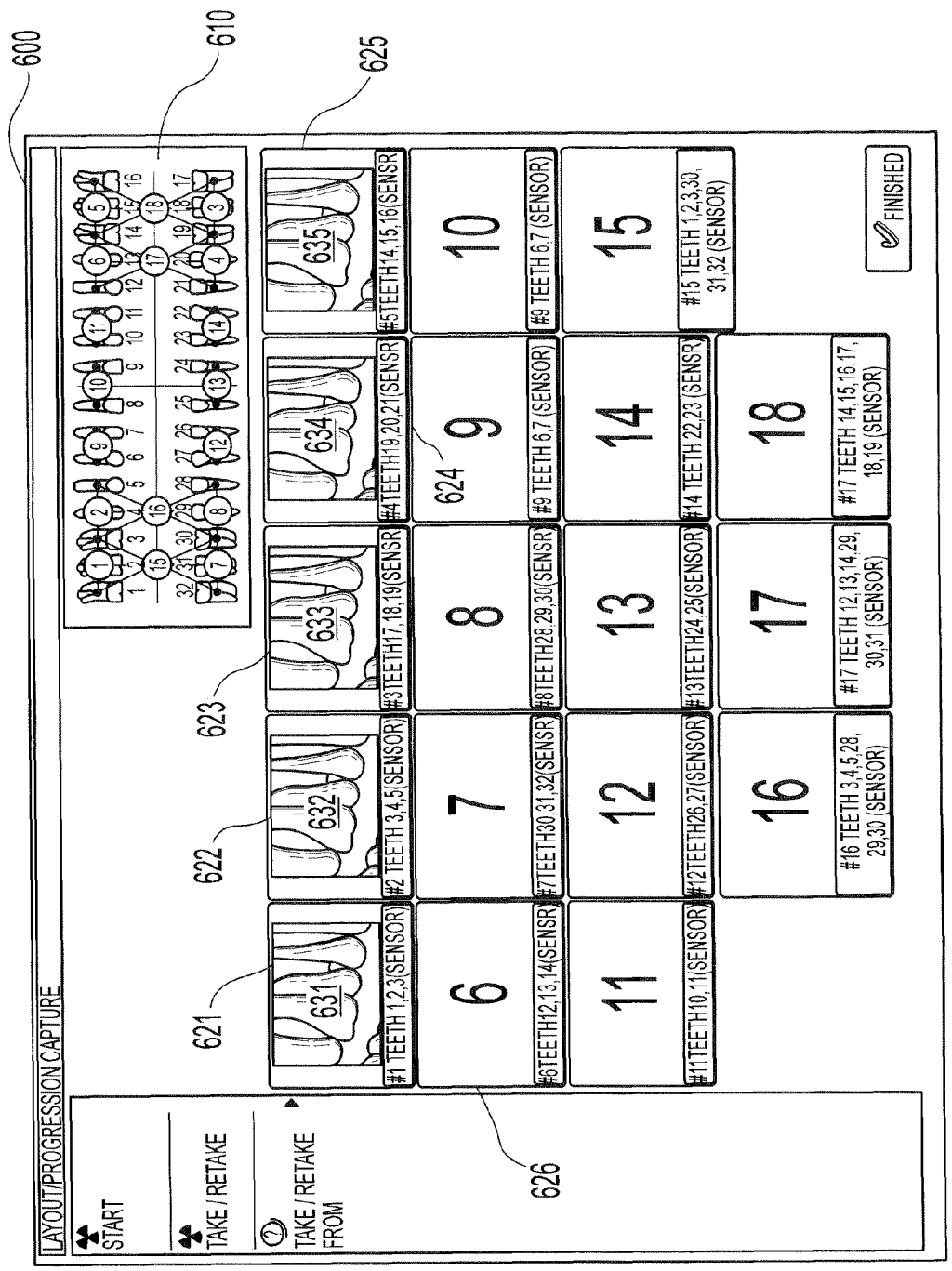
FIG. 6A illustrates an exemplary embodiment of a resultant displayed screen using the method of FIG. 5, in accordance with various aspects of the present invention.

FIG. 6A illustrates an exemplary embodiment of a resultant displayed screen 600 using the method 500 of FIG. 5, in accordance with various aspects of the present invention. The displayed screen 600 includes a tooth progression chart 610 displayed in the upper right corner for a full mouth series of eighteen images (FMX-18). The tooth progression chart 610 includes a set of numbered teeth in anatomically correct relation to each other along with corresponding indicia identifying the eighteen anatomical structures (i.e., eighteen sets of teeth) to be imaged. Displaying the tooth progression chart 610 corresponds to steps 510 and 520 of the method 500.

The vast majority of the displayed screen 600 is dedicated to displaying eighteen image layouts corresponding to the eighteen sets of teeth to be imaged in progressive order 1 to 18. For example, the first five image layouts 621-625 include captured digital images 631-635 corresponding to the first five anatomical structures in the progression as indicated by the numerical indicia in the tooth progression chart 610. In step 530 of the method 500, an imaging device (e.g., an intra-oral digital X-ray device) is positioned within the patient's mouth in order to image the first anatomical structure defined by the tooth progression chart 610. In accordance with an embodiment of the present invention, at least one of the first image layout, the first anatomical structure, and the indicia associated with the first anatomical structure is automatically high-lighted on the display of the computer-based platform when the first image is to be acquired. According to step 540 in the method 500, the first image 631 is acquired and displayed in the first image layout 621. This first image 631 and first image layout 621 correspond to the first anatomical structure defined in the tooth progression chart 610 which corresponds to the teeth numbers 1, 2, and 3.

According to step 550 of the method 500, the imaging device is re-positioned within the patient's mouth in order to image the second anatomical structure defined by the tooth progression chart 610, or a second imaging device may be used. In accordance with an embodiment of the present invention, at least one of the second image layout, the second anatomical structure, and the indicia associated with the second anatomical structure is automatically high-lighted on the display after the first image has been acquired and when the second image is to be acquired. Subsequently, according to step 560 of the method 500, the second image 632 is acquired and displayed in the second image layout 622. This second image 632 and second image layout 622 correspond to the second anatomical structure defined in the tooth progression chart 610 which corresponds to the teeth numbers 3, 4, and 5. As shown in FIG. 6A, the method has been continued to acquire and display three more images 633-635 of the next three anatomical structures defined by the tooth progression chart 610 in their corresponding image layouts 623-625. The method may continue until all eighteen anatomical structures (i.e., predefined sets of teeth) are captured for the FMX-18 series.

Figure 6B:
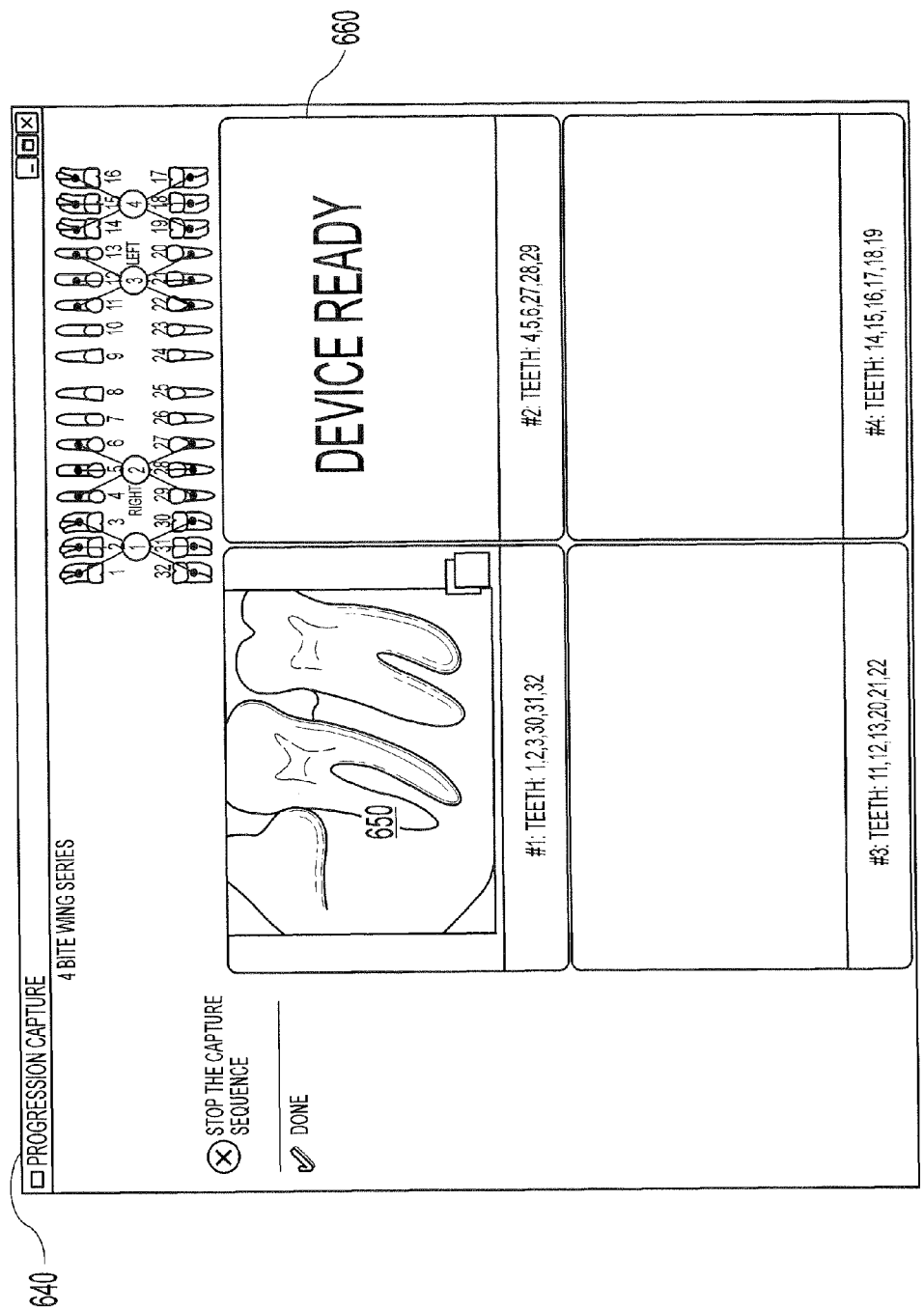
FIG. 6B illustrates an exemplary embodiment of a resultant displayed screen after having captured a first image and when preparing to capture a second image in a second image layout, in accordance with various aspects of the present invention.

Also, various status messages may be displayed in the current image layout. For example, FIG. 6B illustrates an exemplary embodiment of a resultant displayed screen 640 after having captured a first image 650 and when preparing to capture a second image in image layout 660, in accordance with various aspects of the present invention. The status message "Device Ready" is displayed in the image layout 660, indicating to the user that the system is ready to capture the next image. Other status messages are possible as well, in accordance with various embodiments of the present invention.

In accordance with various embodiments of the present invention, a first imaging device of a first type (e.g., a digital X-ray device) may be used to generate and store a first digital image as a first image shot in a progression of image shots, and a second imaging device of a second type (e.g., a digital camera or a digital video camera) may be used to generate and store a second digital image as a second image shot in the same progression of image shots. That is, in general, different image shots within a progression of image shots may correspond to digital images generated using different imaging devices. This brings more flexibility to the user when performing exams or studies.

If a dentist makes a mistake by imaging a wrong anatomical structure (i.e., an anatomical structure that does not correspond to the current image layout with which the image will be associated and displayed), then the dentist can delete the image or move the image. For example, referring to FIG. 6A, if the image 635 really corresponds to teeth numbers 12, 13, and 14 (i.e., image layout 626), then the dentist can use the user interface 130 to select the image 635 and drag it from image layout 625 into image layout 626. Alternatively, the dentist may use the user interface 130 to delete the image 635. Then the dentist may re-position the imaging device and recapture an image for the image layout 625. In general, a user may move any image from one image layout to another, or may delete any image within an image layout. Also, a user may drag multiple images to a "drop area" or a temporary holding location, and then re-order the images in the image layouts. Furthermore, a user may view all of the images, which may not yet be assigned to any image layout, and then select an image to go into a selected image layout. Other methods of arranging and assigning images are possible as well, in accordance with various embodiments of the present invention.

FIG. 7 illustrates a flow chart of an embodiment of a method 700 for viewing a sequence of previously captured anatomical images on the computer-based platform 100 of FIG. 1, in accordance with various aspects of the present invention. In step 710, a pictorial representation of at least two anatomical structures to be viewed on a display of a computer-based platform are displayed such that the at least two anatomical structures are positioned in correct anatomical relation to each other in the pictorial representation. In step 720, at least one indicia for each of the at least two anatomical structures is displayed as part of the pictorial representation on the display of the computer-based platform such that it is apparent which indicia are associated with which anatomical structures. The indicia define an ordered progression in which images associated with the at least two anatomical structures have been previously acquired from a patient using at least one imaging device. In step 730, one image layout for each anatomical structure for which the images have been previously acquired is displayed on the display of the computer-based platform such that it is apparent which anatomical structure is associated with which image layout. In step 740, one of the previously acquired images is displayed within each image layout on the display of the computer-based platform such that each displayed image corresponds to the anatomical structure associated with each image layout. The exact order of the steps 710-740 is not necessarily critical. Other embodiments may re-order and/or combine the steps to achieve a same resultant displayed screen.

Figure 8:
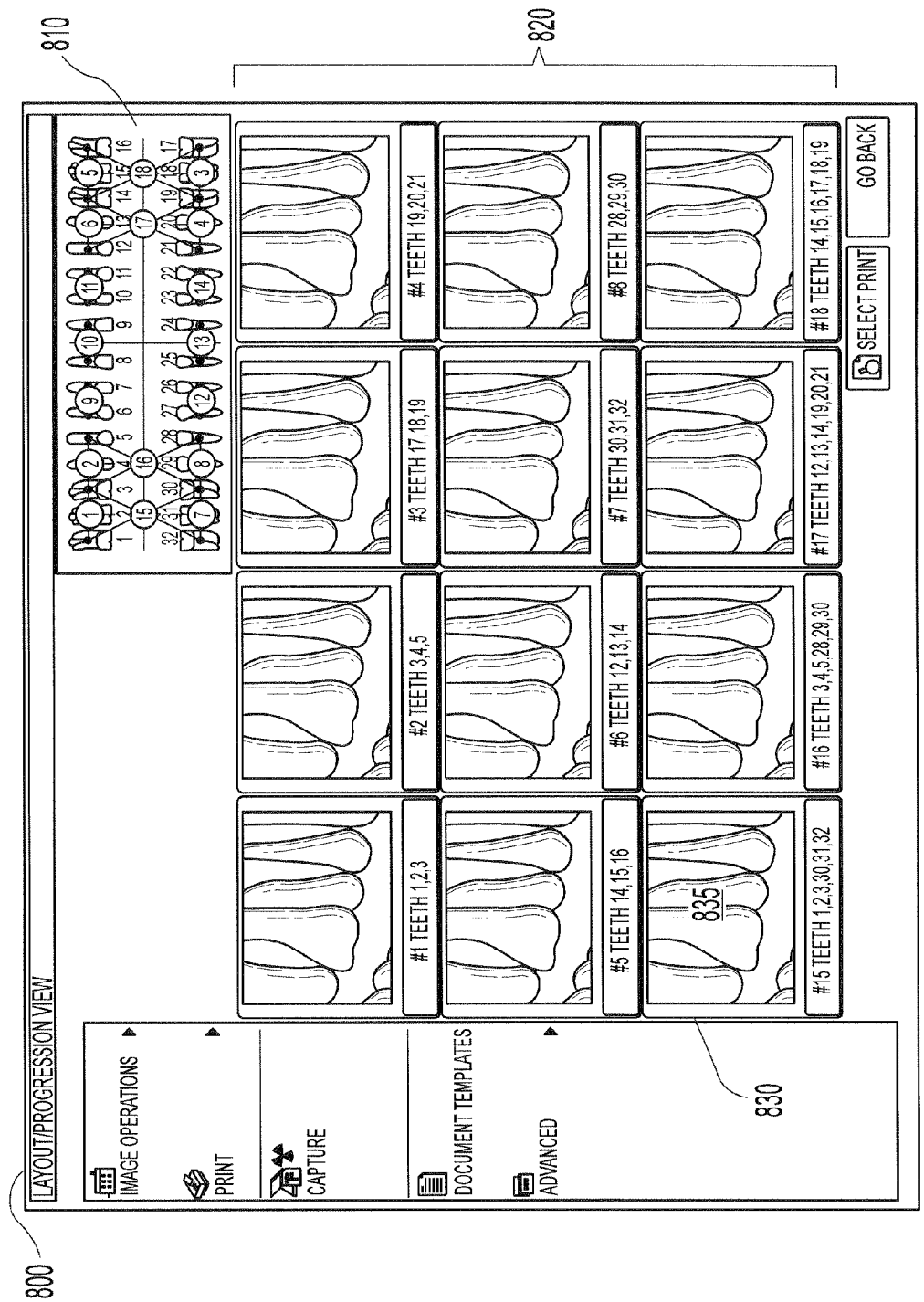
FIG. 8 illustrates an exemplary embodiment of a resultant displayed screen using the method of FIG. 7, in accordance with various aspects of the present invention.

FIG. 8 illustrates an exemplary embodiment of a resultant displayed screen 800 using the method 700 of FIG. 7, in accordance with various aspects of the present invention. The displayed screen 800 includes a tooth progression chart 810 displayed in the upper right corner for a full mouth series of eighteen images (FMX-18). The tooth progression chart 810 includes a set of numbered human teeth in anatomically correct relation to each other along with corresponding indicia identifying the eighteen anatomical structures (i.e., eighteen sets of teeth) to be viewed. Displaying the tooth progression chart 810 corresponds to steps 710 and 720 of the method 700. Notice that any given tooth may be associated with more than one anatomical structure and, therefore, with more than one indicia. For example, tooth number 1 is associated with indicia 1 and indicia 15 (i.e., anatomical structure 1 which includes teeth numbers 1, 2, and 3; and anatomical structure 15 which includes teeth numbers, 1, 2, 3, 30, 31, and 32).

The vast majority of the displayed screen 800 is dedicated to displaying those image layouts with images that have been previously captured. Displaying the image layouts that have corresponding images corresponds to steps 730 and 740 of the method 700. In the displayed screen 800, only twelve image layouts 820, of eighteen possible image layouts, and corresponding twelve images are displayed. The twelve image layouts 820 correspond to twelve of the eighteen anatomical structures in the tooth progression chart 810. In this example, only twelve images were previously captured and stored. Therefore, only twelve images are displayed in the twelve image layouts. For example, the dentist may have had a reason to only capture the images of these twelve anatomical structures and not the other six. Or the dentist may have recently deleted the other six images. In either case, the image layouts 820 and corresponding images are displayed in progression order (1-18) even though progressions 9-14 are not displayed since there are no corresponding images.

In accordance with an embodiment of the present invention, the displayed size of each of the twelve image layouts and corresponding images is adapted to make maximum use of the display screen. For example, if all eighteen image layouts contained images, then all eighteen image layouts would be displayed on the display screen but each image layout would be adapted to be smaller in size to make room for the extra six image layouts to be displayed. Similarly, if fewer than twelve images were available, then the displayed size would be increased for each image layout and corresponding image. In general, the display size of any image layout and associated image is inversely proportional to the number of images to be displayed.

In accordance with an alternative embodiment of the present invention, only one image layout is displayed at a time on the display 160 and the user may use the user interface 130 to scroll through the various image layouts and associated images on the display 160. As a result, the displayed size of each image layout may be fairly large.

Also, a user may use the user interface 130 to select a single image to be displayed from the set of currently displayed image layouts 820. For example, a user (e.g., dentist) may click on image 835 of image layout 830. The image 835 would be increased in size on the display. The other images would not be displayed. Alternatively, the user may click on the corresponding anatomical structure or indicia on the tooth progression chart 810 in order to display a single image. In general, a user may select any number of images to display out of the full set of images available in the progression set or may scroll through the images.

Figure 9:
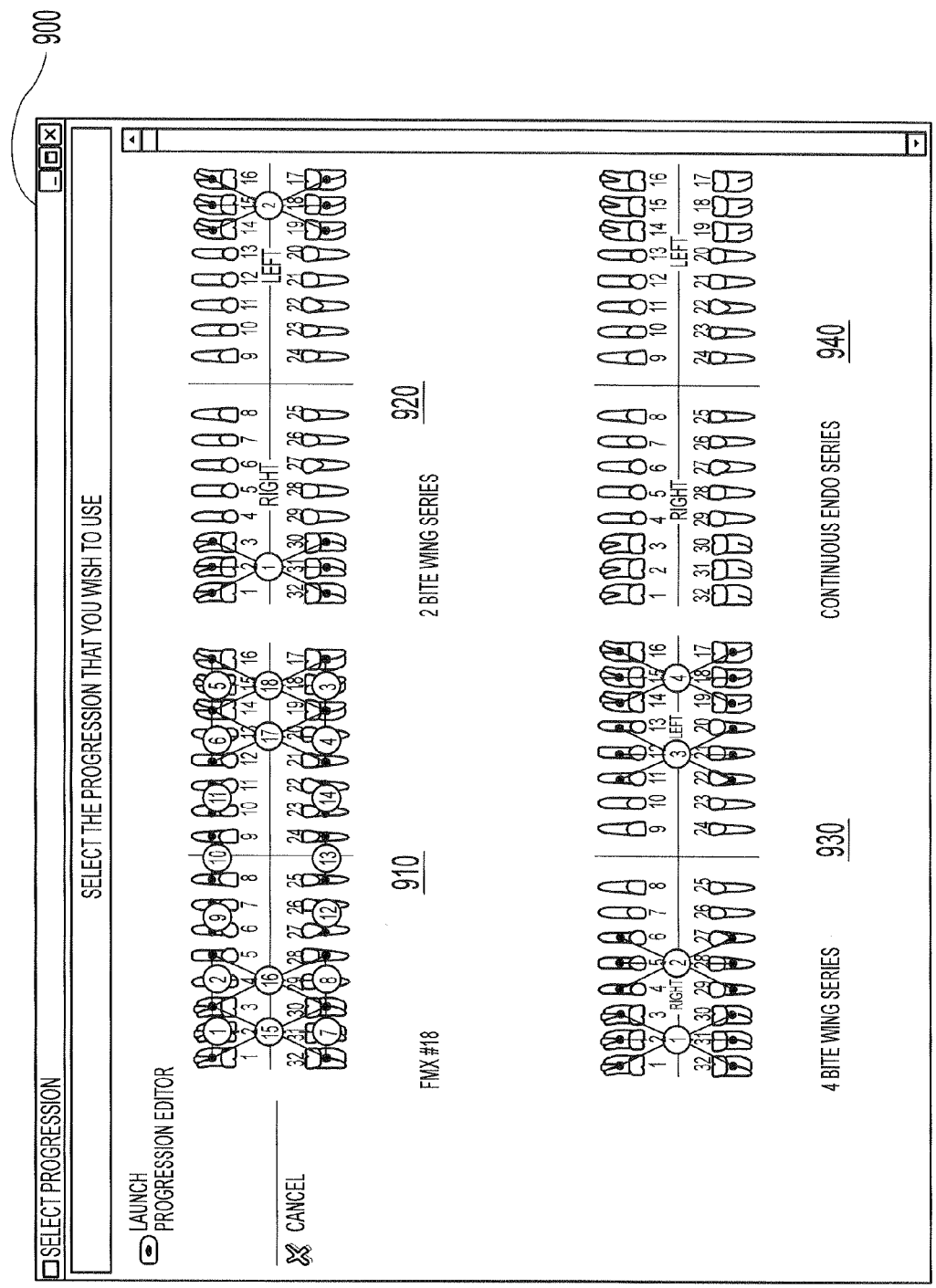
FIG. 9 illustrates an exemplary embodiment of a displayed screen displayed by the system of FIG. 1 showing four choices of progression series in an alternative format to that of FIG. 4, in accordance with various aspects of the present invention.

FIG. 9 illustrates an exemplary embodiment of a displayed screen 900 displayed by the system 100 of FIG. 1 showing four choices of progression series 910, 920, 930, and 940 in an alternative format to that of FIG. 4, in accordance with various aspects of the present invention. The four progression series 910-940 are each displayed as a tooth progression chart in the displayed screen 900. In accordance with an embodiment of the present invention, representations of the progression series (i.e., the tooth progression charts) are displayed in the most-recently used order and are selected by clicking on the respective representation. The first progression series 910 corresponds to a standard FMX series, the second progression series 920 corresponds to a standard 2 bite wing series, the third progression series 930 corresponds to a standard 4 bite wing series, and the fourth progression series 940 corresponds to a continuous endo series. Many other standard and custom series are possible as well in accordance with various embodiments of the present invention.

In accordance with various embodiments of the present invention, mixed dentition may be specified for each image shot within a progression of image shots. A user may also specify an orientation (e.g., left, right) of any of the images to be acquired in a progression using the user interface of the computer-based platform system. The specified orientation is displayed as a part of at least one of the pictorial representation (as shown in FIG. 4) or the associated image layout. Also, the system and methods described herein may be adapted to other forms of medical imaging besides that of dentistry. For example, instead of using a tooth chart, the system and methods may use some other anatomical type of chart (e.g., a chart showing various anatomical structures within a patient's hand).

A system and method for capturing and displaying images in an ordered manner are also disclosed. An image progression description (IPD) is generated using an independent imaging software application (ISA). The IPD defines an ordered sequence of image acquisition instruction sets (IAIS) and an image display layout (IDL). The ordered sequence of IAIS is transferred to a portable image acquisition device (PIAD) which reads and sequentially displays the ordered sequence of IAIS. A plurality of images (e.g., digital images) is acquired using the PIAD in accordance with the ordered sequence of IAIS. The plurality of images are transferred back to the ISA and are displayed according to the IDL. The user of the PIAD may be considered a third party to the user of the ISA.

Figure 10:
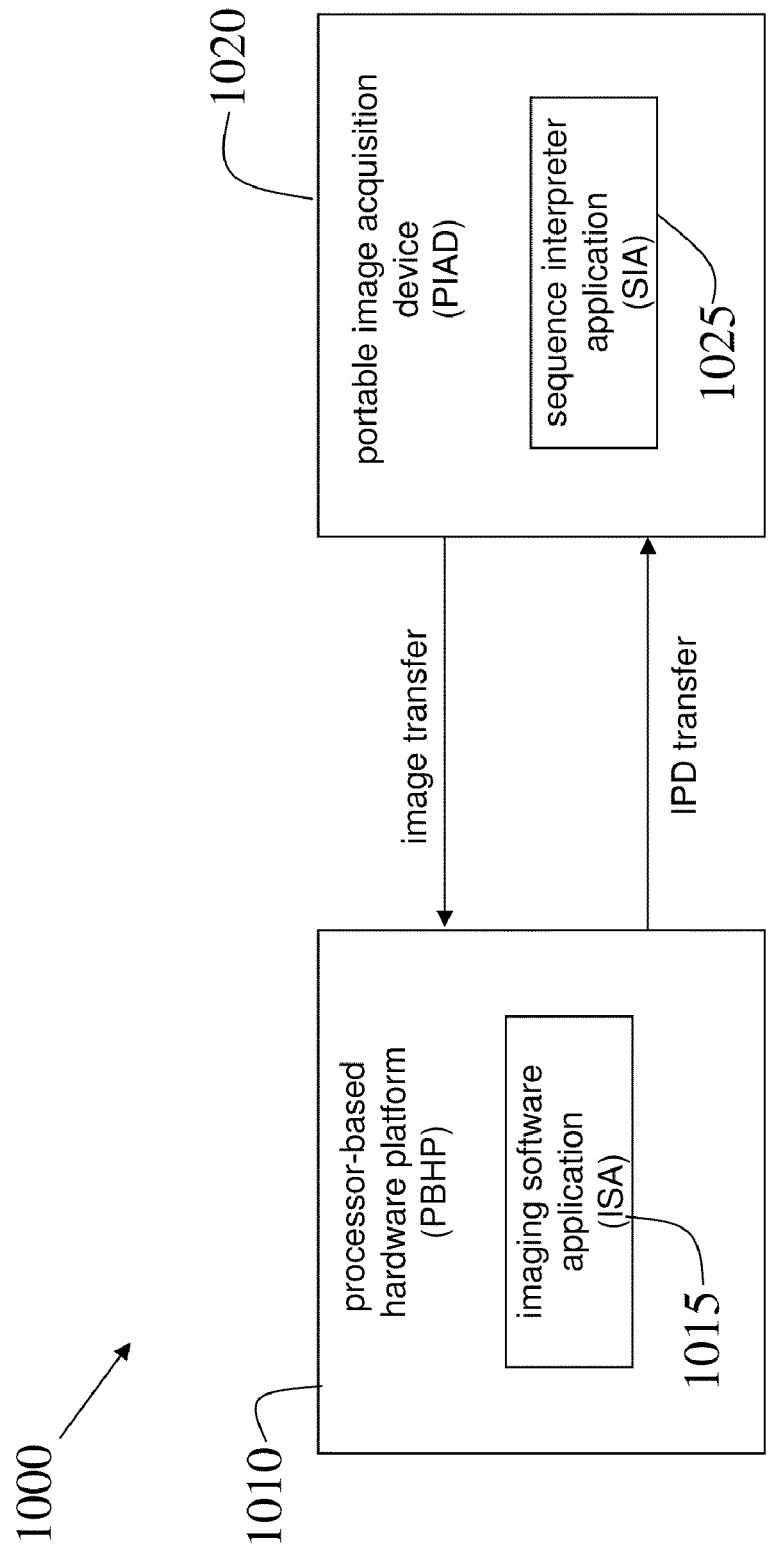
FIG. 10 illustrates an example embodiment of a system for capturing and displaying images in an ordered manner.

FIG. 10 illustrates an example embodiment of a system 1000 for capturing and displaying images in an ordered manner. The images may be any type of images such as, for example, digital medical images or structural images (e.g., images of portions of a structure of a bridge). The system includes a processor-based hardware platform (PBHP) 1010 and an imaging software application (ISA) 1015 capable of running on the PBHP 1010. In accordance with an embodiment of the present invention, the PBHP 1010 is a personal computer (PC) having at least one microprocessor and memory. The ISA 1015 may be stored in memory on the PC or loaded from, for example, a storage disk. The ISA 1015 running on the PBHP 1010 is capable of being used to generate an image progression description (IPD) and display images, as described in more detail later herein.

The system 1000 also includes a portable image acquisition device (PIAD) 1020 capable of communicating with the PBHP 1010 to receive an IPD or at least a portion of an IPD. The PIAD 1020 is further capable of acquiring images according to a defined ordered sequence and transferring the images to the PBHP 1010. In accordance with various embodiments of the present invention, the PIAD 1020 may include a digital camera, a medical imaging device (e.g., a portable ultrasound device), or some other type of portable imaging device.

Figure 11:
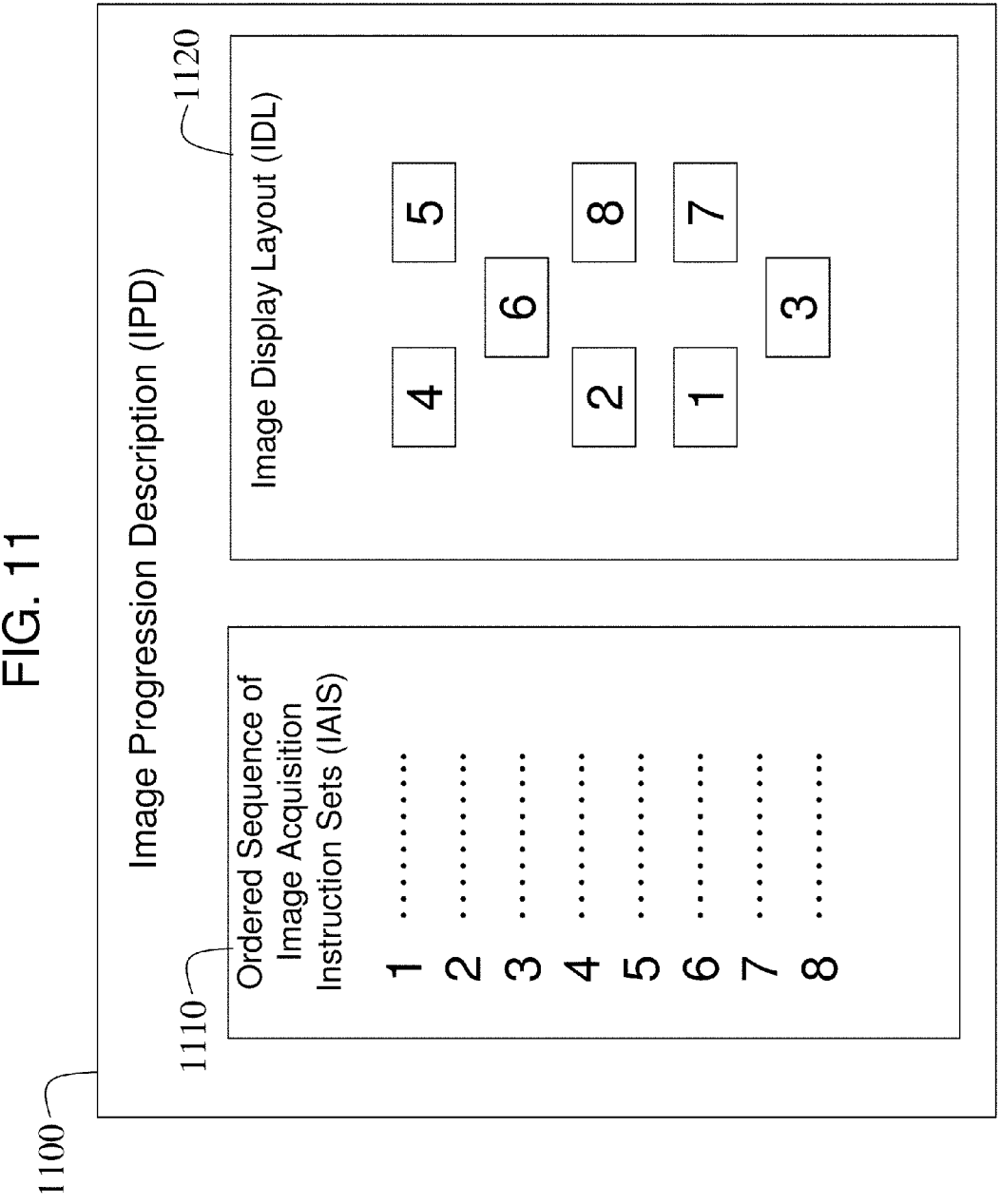
FIG. 11 illustrates an example embodiment of an image progression description (IPD) generated using the system of FIG. 10.

FIG. 11 illustrates an example embodiment of an image progression description (IPD) 1100 generated using the system 1000 of FIG. 10. A user, using the ISA 1015 on the PBHP 1010 is able to generate an IPD (e.g., IPD 1100). The IPD 1100 has two main parts including an ordered sequence of image acquisition instruction sets (IAIS) 1110 and an image display layout (IDL) 1120. FIG. 11 shows an ordered sequence of eight instructions sets. Each instruction set of the IAIS 1110 includes individual instructions (represented as dots in FIG. 11) for how to acquire an image (e.g., see FIG. 13). The IDL 1120 defines how the eight images, acquired in accordance with the IAIS 1110, are to be displayed in relation to each other. In accordance with an embodiment of the present application, the ISA 1015 assigns or tags an identifying code to the IPD 1100 (e.g., electronically assigns or tags).

In accordance with an embodiment of the present invention, the IAIS 1110 (and the identifying code) is transferred (IPD transfer . . . see FIG. 10) from the PBHP 1010 to the PIAD 1020 and used by a user of the PIAD 1020 to acquire images in accordance with the ordered sequence of IAIS 1110. The IDL 1120 defines how the acquired images will be displayed at the PBHP 1010 after being acquired by the PIAD 1020 and transferred back to the PBHP 1010 (image transfer . . . see FIG. 10). At the PIAD 1020, the acquired images are also tagged with the identifying code of the IPD such that the ISA 1015 is able to associate the IDL of the IDP with the plurality of acquired images based on the identifying code.

Figure 12:
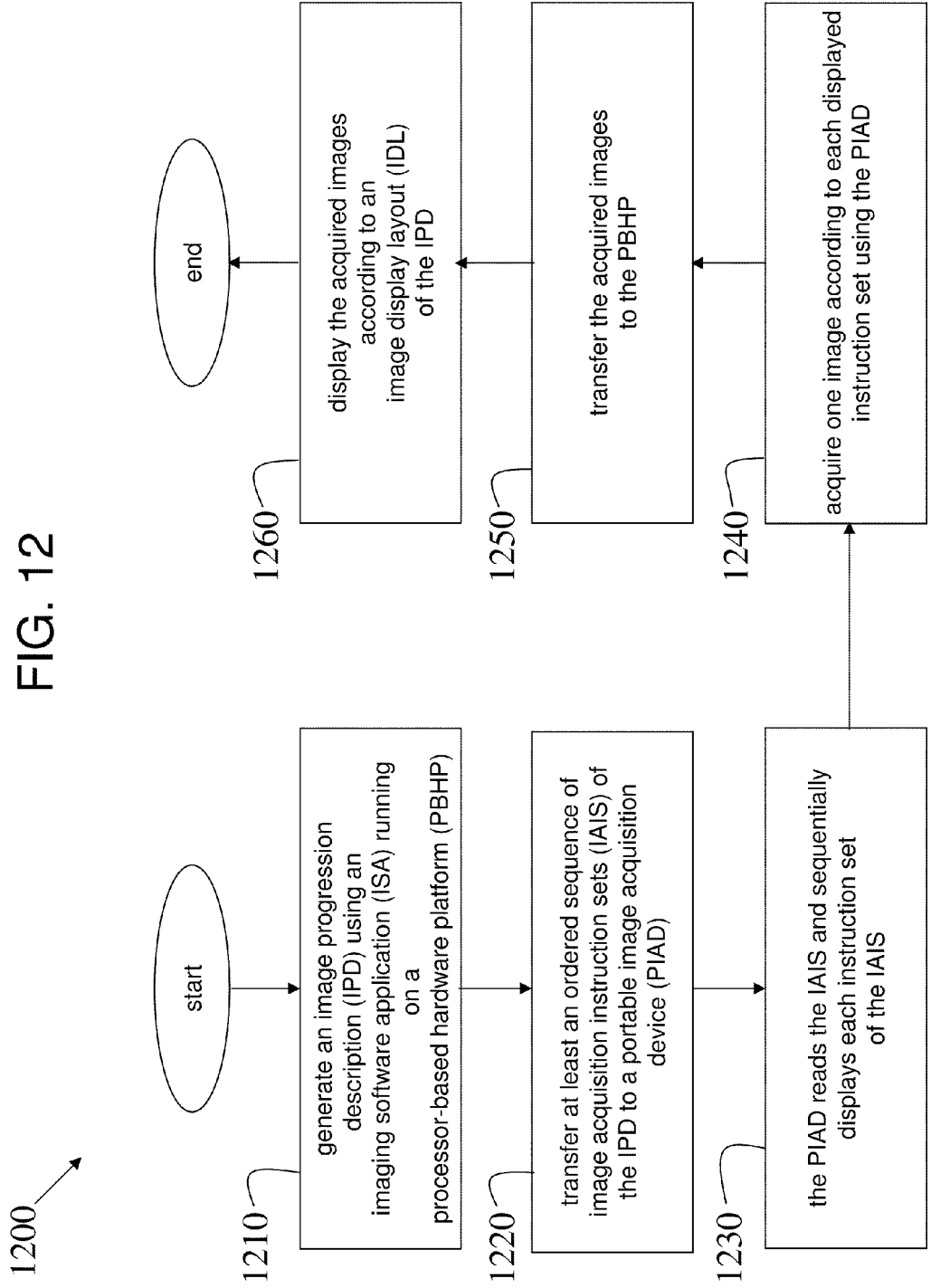
FIG. 12 is a flowchart of an example embodiment of a method of capturing and displaying images in an ordered manner, using the system of FIG. 10.

FIG. 12 is a flowchart of an example embodiment of a method 1200 of capturing and displaying images in an ordered manner, using the system 1000 of FIG. 10. In step 1210, generate an image progression description (IPD) using an imaging software application (ISA) running on a processor-based hardware platform (PBHP), wherein the image progression description (IPD) defines an ordered sequence of image acquisition instruction sets (IAIS) and an image display layout (IDL). In step 1220, transfer at least the IAIS portion of the IPD to a portable image acquisition device (PIAD). In step 1230, the PIAD reads at least the transferred ordered sequence of IAIS portion of the IPD and sequentially displays each instruction set of the IAIS. Each next instruction set may be displayed, one at a time, after each previous image has been acquired. Alternatively, all of the instructions sets may be displayed at the same time, in ordered sequence. In step 1240, acquire a single image, using the PIAD, in accordance with each instruction set of the ordered sequence of IAIS, thereby acquiring a plurality of images. In step 1250, transfer the plurality of images to the PBHP and, in step 1260, display the plurality of images according to the IDL of the IPD.

In accordance with an embodiment of the present application, the PIAD 1020 includes a sequence interpreter application (SIA) 1025 capable of reading an IAIS. The SIA 1025 may be capable of reading a standard IAIS format, or may be capable of reading a customized IAIS format, or many different standard or customized IAIS formats. For example, the PBHP 1010 may know to transfer the IAIS in a particular format that is compatible with the PIAD 1020. For example, if a user of the PBHP 1010 selects the type of PIAD 1020 using the ISA 1015, then the ISA 1015 formats the IAIS in a compatible format.

FIG. 13 illustrates an example embodiment of an ordered sequence of image acquisition instruction sets (IAIS) 1300 generated using the system 1000 of FIG. 10 and the method 1200 of FIG. 12. The IAIS 1300 includes an ordered sequence of four sets of instructions 1301-1304 for instructing, for example a dental technician, how to acquire a four bite wing series of images from a patient. Each of the instruction sets 1301-1304 includes an image acquisition number, an anatomic region, and an orientation. The image acquisition number indicates the numbered position of the image to be acquired in the ordered sequence (e.g., #1, #2, #3, #4). The anatomic region indicates which teeth are to be imaged (e.g., by teeth #). The orientation indicates how the dental technician is to position the imaging sensor of the PIAD (e.g., a portable X-ray device).

In accordance with another embodiment of the present invention, each image acquisition instruction set 1301-1304 may further include a sensor type, indicating to the dental technician which type or size of digital imaging sensor to use to acquire each image. Other additional instructions may be included as well, in accordance with other alternative embodiments of the present invention. For example, for a structural scenario such as inspecting a bridge, instead of each instruction set including an anatomic region, each instruction set may include a structural region of the bridge.

As an example, referring to FIG. 10 and FIG. 13, a dentist at a dental office uses the PBHP 1010 (e.g., a PC), having the ISA 1015, to generate an IPD having the ordered sequence of IAIS 1300 and a IDL (not shown). The dentist then transfers the IPD, or at least the IAIS 1300, (e.g., as a formatted file) to a PIAD 1020 (e.g., a portable dental X-ray device) to be used by a dental technician in the field (e.g., at a remote location in a poor neighborhood). The IPD or IAIS 1300 may be transferred, for example, through a cellular telephone network. Other wired or wireless means of transfer are possible as well such as, for example, through the internet.

Continuing with the example, the IAIS 1300 are received by the PIAD 1020 and read and displayed by the PIAD 1020 (e.g., on a LCD display of the PIAD) such that the dental technician can view the instructions in their ordered sequence, either one instruction set at a time or all at once. The dental technician is cued by the IAIS to follow the instructions of the IAIS 1300 to acquire a single image for each instruction set of the IAIS 1300 in the ordered sequence or progression. The ordered sequence may be the most efficient way to acquire the images, for example, for the patient. The PIAD 1020 then transfers the images back to the PBHP 1010 (e.g., via the cellular telephone network or the internet) to be displayed to the dentist on a display of the PBHP 1010 according to the IDL of the IPD. The images may be transferred to the PBHP 1010 all at once via a batch transfer process after all the images are acquired. Alternatively, the images may be transferred to the PBHP 1010, one at a time, via a real time transfer process subsequent to acquiring each image but before acquiring a next image.

The IDL could be very different from the ordered sequence, or could closely follow the ordered sequence, in accordance with various embodiments of the present invention. For example, the IDL may provide a most efficient or desired way to view the images, even though the ordered sequence provides a most efficient way to acquire the images. In this manner, a dentist at his office can direct a dental technician in the field to acquire the images in a very particular manner, and have the images displayed back to the dentist in another very particular manner, for example.

As another example, a state bridge inspector at a state office uses the PBHP 1010 (e.g., a workstation), having the ISA 1015, to generate an IPD having an ordered sequence of IAIS and a IDL. The bridge inspector then transfers the IPD, or at least the IAIS (e.g., as a file) to a PIAD 1020 (e.g., a portable digital camera device) to be used by a construction worker in the field (e.g., at a bridge on a major highway). The IPD or IAIS may be transferred, for example, through a satellite communication network. Other wired or wireless means of transfer are possible as well such as, for example, through the internet.

Continuing with the example, the IAIS are received by the PIAD 1020 and read and displayed by the PIAD 1020 (e.g., on a LED display of the PIAD) such that the construction worker can view the instructions in their ordered sequence, either one instruction set at a time or all at once. The construction worker then follows the instructions of the IAIS to acquire a single image for each instruction set of the IAIS in the ordered sequence or progression. The ordered sequence may be the most efficient way to acquire the images, for example, based on the design and construction of the bridge. The PIAD 1020 then transfers the images back to the PBHP 1010 (e.g., via the satellite communication network or the internet) to be displayed to the state bridge inspector on a display of the PBHP 1010 according to the IDL of the IPD.

Again, the IDL could be very different from the ordered sequence, or could closely follow the ordered sequence, in accordance with various embodiments of the present invention. For example, the IDL may provide a most efficient or desired way to view the images, even though the ordered sequence provides a most efficient way to acquire the images. In this manner, a bridge inspector at his office can direct a construction worker in the field to acquire the images in a very particular manner, and have the images displayed back to the bridge inspector in another very particular manner, for example.

In accordance with one alternative embodiment of the present invention, the PIAD may actually be two devices capable of communicating with each other. The first device of the PIAD is capable of reading the transferred IAIS portion of the IPD, and sequentially displaying each instruction set of the IAIS. The second device of the PIAD is capable of acquiring images according to the instruction sets of the IAIS. For example, the first device may be a cellular telephone device co-located with and in wireless communication (e.g., via a Bluetooth® connection) with the second device which may be a digital camera.

In general, the PIAD may be located remotely from the PBHP. Alternatively, the PIAD may be co-located with the PBHP, for example, in a same office or facility. For example, a medical doctor may use the PBHP in his office to construct a number of IPD's, each for a different patient, and then later transfer and use the ordered sequence of IAIS to image the patients at different times of the day when the patients arrive for their respective appointments. In such a co-located scenario, the PIAD may be hard-wired to the PBHP via a connector cable (e.g., a USB cable), or the PIAD may be capable of wirelessly communicating with the PBHP via a wireless Bluetooth® connection, for example. As an alternative, an IPD (or at least an IAIS) may be transferred from the PBHP to the PIAD via a memory card. Similarly, acquired digital images may be transferred from the PIAD to the PBHP via a memory card.

In accordance with other embodiments of the present invention, a user of the ISA 1015 may generate an ordered sequence of IAIS and not generate an IDL, or generate an IDL later (e.g., after the images have been acquired according to the IAIS). Similarly, a user of the ISA 1015 may generate an IDL without generating an ordered sequence of IAIS, such as in the case where images were previously acquired in some other manner, or the user may generate the IAIS later in anticipation of acquiring the images at a later time.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A method of capturing and displaying images in an ordered manner, said method comprising:
   generating an image progression description (IPD) using an imaging software application (ISA) running on a processor-based hardware platform (PBHP), wherein said image progression description (IPD) defines an ordered sequence of image acquisition instruction sets (IAIS) and an image display layout (IDL);
   transferring at least said ordered sequence of image acquisition instruction sets (IAIS) portion of said image progression description (IPD) to a portable image acquisition device (PIAD);
   said portable image acquisition device (PIAD) reading at least said transferred ordered sequence of image acquisition instruction sets (IAIS) portion of said image progression description (IPD), and sequentially displaying each instruction set of said ordered sequence of image acquisition instruction sets (IAIS);
   acquiring a single image, using said portable image acquisition device (PIAD), in accordance with each instruction set of said ordered sequence of image acquisition instruction sets (IAIS), thereby acquiring a plurality of images;
   transferring said plurality of images to said processor-based hardware platform (PBHP); and
   displaying said plurality of images according to said image display layout (IDL).

2. The method of claim 1 further comprising said imaging software application (ISA) associating said plurality of images with said image display layout (IDL) based on an identifying code with which said plurality of images and said image progression description (IPD) are each electronically tagged.

3. The method of claim 1 further comprising said imaging software application (ISA) electronically tagging said image progression description (IPD) with an identifying code before said image progression description (IPD) is transferred.

4. The method of claim 3 further comprising said portable image acquisition device (PIAD) electronically tagging said plurality of images with said identifying code before said plurality of images are transferred.

5. The method of claim 1 wherein said plurality of images are transferred via a batch transfer process.

6. The method of claim 1 wherein each single image of said plurality of images is transferred via a real time transfer process subsequent to acquiring said each single image and before acquiring a next single image of said plurality of images.

7. The method of claim 1 wherein each instruction set of said ordered sequence of image acquisition instruction sets includes an image acquisition number, identification of an anatomic region to be imaged, and acquisition orientation information.

8. The method of claim 1 wherein each instruction set of said ordered sequence of image acquisition instruction sets includes an image acquisition number, identification of a structural region to be imaged, and acquisition orientation information.

9. The method of claim 1 wherein said processor-based hardware platform (PBHP) is co-located with said portable image acquisition device (PIAD).

10. The method of claim 1 wherein said portable image acquisition device (PIAD) is located remotely from said processor-based hardware platform (PBHP).

11. A system for capturing and displaying images in an ordered manner, said system comprising:
    means for generating an image progression description (IPD), wherein said image progression description (IPD) defines an ordered sequence of image acquisition instruction sets (IAIS) and an image display layout (IDL);
    means for transferring at least said ordered sequence of image acquisition instruction sets (IAIS) portion of said image progression description (IPD);
    means for reading at least said transferred ordered sequence of image acquisition instruction sets (IAIS) portion of said image progression description (IPD) and sequentially displaying each instruction set of said ordered sequence of image acquisition instruction sets (IAIS);
    portable means for acquiring a single image in accordance with each instruction set of said ordered sequence of image acquisition instruction sets (IAIS), thereby allowing acquisition of a plurality of images;
    means for transferring said plurality of images; and
    means for displaying said plurality of images according to said image display layout (IDL).

12. The system of claim 11 further comprising means for associating said plurality of images with said image display layout (IDL) based on an identifying code with which said plurality of images and said image progression description (IPD) are each electronically tagged.

13. The system of claim 11 further comprising means for electronically tagging said image progression description (IPD) with an identifying code before said image progression description (IPD) is transferred.

14. The system of claim 13 further comprising means for electronically tagging said plurality of images with said identifying code before said plurality of images are transferred.

15. The system of claim 11 wherein said means for transferring said plurality of images employs a batch transfer process.

16. The system of claim 11 wherein said means for transferring said plurality of images employs a real time transfer process wherein each single image of said plurality of images is transferred subsequent to acquiring said each single image and before acquiring a next single image of said plurality of images.

17. The system of claim 11 wherein each instruction set of said ordered sequence of image acquisition instruction sets (IAIS) includes an image acquisition number, identification of an anatomic region to be imaged, and acquisition orientation information.

18. The system of claim 11 wherein each instruction set of said ordered sequence of image acquisition instruction sets (IAIS) includes an image acquisition number, identification of a structural region to be imaged, and acquisition orientation information.

19. The system of claim 11 wherein said means for generating an image progression description (IPD) is co-located with said portable means for acquiring.

20. The system of claim 11 wherein said portable means for acquiring is located remotely from said means for generating an image progression description (IPD).

21. The system of claim 11 wherein said means for reading and sequentially displaying is co-located with said portable means for acquiring.

* * * * *